(12) United States Patent
Nakamura et al.

(10) Patent No.: US 6,370,941 B2
(45) Date of Patent: Apr. 16, 2002

(54) GAS SENSOR AND GAS SENSOR SYSTEM

(75) Inventors: Michihiro Nakamura; Yuko Nagai; Tetsushi Sekiguchi, all of Tokyo (JP)

(73) Assignee: Nihon Kohden Corporation, Tokyo (JP)

( * ) Notice: Subject to any disclaimer, the term of this patent is extended or adjusted under 35 U.S.C. 154(b) by 0 days.

(21) Appl. No.: 09/775,624

(22) Filed: Feb. 5, 2001

(30) Foreign Application Priority Data

Feb. 3, 2000 (JP) ........................................ 2000-026045

(51) Int. Cl.[7] ........................ G01N 27/46; G01N 27/26; B32B 27/04; A61B 5/00
(52) U.S. Cl. .................... 73/31.05; 73/53.01; 73/61.41; 73/23.2; 422/82.04; 324/438
(58) Field of Search ................................ 73/31.05, 23.2, 73/23.34, 53.01, 61.41; 422/82.03, 82.04, 56–57; 324/438 T, 444, 926

(56) References Cited

U.S. PATENT DOCUMENTS

| | | | | |
|---|---|---|---|---|
| 2,787,903 A | * | 4/1957 | Beard | 73/23 |
| 3,040,561 A | * | 6/1962 | Wright | 73/23 |
| 3,437,446 A | * | 4/1969 | Pierce | 23/232 |
| 3,567,383 A | * | 3/1971 | Langley et al. | 23/230 |
| 3,659,586 A | | 5/1972 | Johns et al. | 128/2 E |
| 3,869,354 A | | 3/1975 | Montalvo, Jr. | 204/1 T |
| 4,043,178 A | * | 8/1977 | Winslow, Jr. | 73/23 |
| 4,149,949 A | | 4/1979 | Buzza et al. | 204/195 P |
| 4,373,375 A | * | 2/1983 | Jerhune et al. | 73/19 |
| 4,490,234 A | | 12/1984 | Buzza | 204/409 |
| 4,736,748 A | | 4/1988 | Nakamura et al. | 128/632 |
| 5,033,321 A | * | 7/1991 | Gerson | 73/866 |
| 5,106,755 A | * | 4/1992 | Tanaka | 436/137 |
| 5,131,260 A | * | 7/1992 | Brand et al. | 73/23.2 |
| 5,325,709 A | * | 7/1994 | Lee | 73/61.43 |
| 5,474,660 A | * | 12/1995 | Robins et al. | 204/153.14 |
| 5,571,944 A | * | 11/1996 | Pfeifer et al. | 73/24.04 |
| 5,952,558 A | * | 9/1999 | Knoblach et al. | 73/40.5 R |
| 5,969,223 A | | 10/1999 | Nagai et al. | 73/1.06 |
| 6,065,329 A | * | 5/2000 | Fukada et al. | 73/40 |
| 6,114,943 A | * | 9/2000 | Lauf | 338/34 |
| 6,119,508 A | * | 9/2000 | Jarui et al. | 73/53.01 |
| 6,277,329 B1 | * | 8/2001 | Evans | 422/80 |

FOREIGN PATENT DOCUMENTS

| | | | |
|---|---|---|---|
| EP | 0 354 604 A2 | 2/1990 | G01N/27/416 |
| EP | 0 478 048 A2 | 4/1990 | G01N/33/49 |
| JP | 4-17050 | 3/1992 | A61B/5/14 |
| JP | 11-70084 | 3/1999 | A61B/5/00 |

OTHER PUBLICATIONS

Elsevier Science S.A.; Atsushi Saito, et al.; "An ISFET Glucose Sensor with a Silicone Rubber Membrane for Undiluted Serum Monitoring"; 1994; pp. 125–129.

* cited by examiner

*Primary Examiner*—Hezron Williams
*Assistant Examiner*—David J. Wiggins
(74) *Attorney, Agent, or Firm*—Sughrue Mion, PLLC (57) ABSTRACT

The conduit tube 3 and the conduit tube 4 to flow the carrier solution to the gas exchanger 7 are provided, and in the conduit tube 3, the reference pH electrode 14 is provided, and in the conduit tube 4, the measuring pH electrode 16 is provided, both pH electrodes preferably being chosen of the ISFET type (Ion-Sensitive Field-Effect-Transistor). The gas exchanger 7 is partitioned from the outside by the gas permeable membrane 6. Initially, the gas exchange section 1 is inserted into the test substance, and next, the carrier solution is flowed at the speed of a degree in which the gas exchange is not conducted in the gas exchanger 7. The output potential difference $\Delta V(0)$ between the reference pH electrode 14 and the measuring pH electrode 16 at this time, is found. Next, the carrier solution is slowly flowed at a predetermined speed, so that the gas exchange is fully conducted in the gas exchanger 7, the output potential difference $\Delta V(t)$ between the reference pH electrode 14 and the measuring pH electrode 16 at time t is found, and the difference $\Delta\Delta V(t)$ between the $\Delta V(t)$ measured at this time and the $\Delta V(0)$ obtained at the last time, is obtained. This value corresponds to the correct gas partial pressure change.

12 Claims, 8 Drawing Sheets

GAS SENSOR AND GAS SENSOR SYSTEM

BACKGROUND OF THE INVENTION

1. Field of Invention

The present invention relates to a gas sensor based on a pH electrode which is used in the fields of medical care and chemical engineering.

2. Related Art

Any one of the conventional gas sensor in which the pH electrode (including an ion sensitive field effect transistor (ISFET)) is its fundamental, has the inner solution suitable for a gas to be measured, the pH electrode, and a reference electrode immersed in the inner solution, and these are covered by a gas permeable membrane. The composition of the inner solution is selected so that, when the gas to be measured is dissolved in the inner solution, the pH is changed.

For example, when the gas to be measured is carbon dioxide or ammonia, H+ ion or OH– ion is generated by the following equilibrium reaction, causing the pH change of the solution. Herein, HCO3– or NH4+ ion which is an ionic species generated when a gas molecule is dissolved in the water, is respectively called a conjugate ion to the carbon dioxide or ammonia. Normally, as the inner solution of the gas sensor based on the pH electrode, a water solution including the excessive conjugate ions to the gas to be measured is used.

$$CO_2+H_2O \rightarrow HCO_3^-+H^+ \quad (1)$$

$$NH_3+H_2O \rightarrow NH_4^++OH^- \quad (2)$$

Further, for the purpose that the pH electrode is operated, the reference electrode is necessary, and in many cases, as the reference electrode, a silver wire (Ag/AgCl) whose surface is chlorinated, is used. Because the potential of this electrode is determined by the concentration of the chloride ion in the solution, normally, in the inner solution, the chloride ion of a predetermined concentration is included other than the conjugate ion.

The gas sensor of the above-described principle is generally called Severinghaus type gas sensor. The measurement result of the severinghaus type gas sensor is displayed normally as the gas partial pressure. When the conjugate ion excessively exists in the inner solution, the following relationship exists between the partial pressure of the gas to be measured and the pH of the inner solution. In the case of acidic gas, $$pH=A-\log Pa \quad (3),$$

in the case of basic gas, $$pH=B+\log Pb \quad (4)$$

Herein, Pa and Pb are respectively the partial pressure of acidic gas and basic gas, and A and B are constants. Hereinafter, the relational expression between the partial pressure of the gas and the output voltage of the pH electrode in the case of the acidic gas will be deriverd.

Generally, between the output voltage V of the pH electrode and the pH, the expression (5) is generally established.

$$V=V0+S(pH-pH0) \quad (5)$$

Herein, S is the pH sensitivity of the pH electrode, and pH0 and V0 are the pH of the inner solution and the output voltage of the pH electrode when the partial pressure of the gas is Pa0. Further, pH and V are the pH of the inner solution and the output voltage when the partial pressure of the gas is Pa. From the expressions (3) and (5), it is clear that the following relationship is derived between the pH electrode and the partial pressure of the gas.

$$V=V0-S(\log Pa-\log Pa0) \quad (6)$$

From this, $$\log Pa=\log Pa0-(V-V0)/S \quad (7)$$

The expression (7) can be generalized as the expression (8).

$$\log Pa=C-V/S \quad (8)$$

Herein, C is a proper constant of the sensor.

From the expression (8), in order to convert the output V of the pH electrode into the partial pressure Pa of the gas, the following can be understood: it is necessary that the two constants C and S are predetermined. To find C and S respectively corresponds to the zero point calibration and the sensitivity calibration. That is, in the same manner as in each kind of other sensor, also when the partial pressure of the gas is measured by using the severinghaus type gas sensor, it is inevitable to conduct the zero point calibration, and the sensitivity calibration. Further, when the temperature of the sensor changes at the time of the calibration and the measurement, it is also necessary to conduct the temperature compensation.

As described above, in the use of Severinghaus type gas sensor, or generally, of the chemical sensors, the two calibrations are inevitable, and the most troublesome matter for putting it to practical use.

In this connection, generally, the pH sensitivity of the pH electrode is theoretically given by following expression (9) of the Nernst' equation.

$$S=2.303RT/F \quad (9)$$

Herein, R is a gas constant, T is absolute temperature, F is a Faraday constant, and when each constant is substituted in this equation, S at 25° C. is 59 mV/pH. Then the equation (9) can be expressed as the expression (10).

$$S=59(273+t)/298 \text{ (mV/pH)} \quad (10)$$

Herein, t is the temperature (° C.). When S is calculated from this expression, for example, it can be found that, when the temperature changes from 0° C. to 40° C., the pH sensitivity increases from 54 to 62 mV/pH. As described above, the sensitivity of the pH electrode is theoretically a function of only the temperature, and in many cases, the actual pH electrode has the sensitivity near the above theoretical value, and its time-dependent change is small. On the one hand, in many cases, there is a case where, for the zero point of the sensor, its time-dependent change can not be negligible.

Based on the above-mentioned trend, there are many cases to apply a method in which, for the sensitivity, the value measured in advance by the manufacturer of the sensor is used, and only the zero point calibration is conducted by the user, or the sensitivity calibration and the zero point calibration are conducted by the user with the sensitivity calibration being less often conducted than the zero point calibration. Specifically, as in the case of a $PCO_2$ sensor for medical care with the comparatively narrower measuring range of $PCO_2$, there is a case in which the necessary accuracy is secured only by the zero point calibration. In JP-A-11-070084, a package for a gas sensor is proposed for simply conducting such a zero point calibration. According to this, by delivering a package of laminated aluminum film in which both of the carbon dioxide of the predetermined partial pressure and the $PCO_2$ sensor are accommodated as a product, the user can conduct the zero point calibration before the user opens the sensor package.

However, in the above gas package system, when the package is once opened, the zero point calibration can not be conducted. That is, although the zero point calibration can be conducted only once before the start of use, the zero point calibration can not be conducted thereafter. On the other side a sensor system by which the zero point calibration can be repeatedly conducted, is disclosed in JP-B-4-017050. This sensor system is the system in which a carrier solution (corresponds to the inner solution of the Severinghaus type gas sensor) is circulated in a gas exchange catheter located in the blood vessel, and the pH electrode is located at the downstream side of the gas exchange catheter, and the partial pressure of the gas is found from the pH of the carrier solution after the gas exchange. In this method, for example, by making the carrier solution flow at so high flow rate that the gas exchange in the gas exchange catheter may be negligible, the carrier solution in which the gas is hardly solved comes into contact with the pH electrode, thereby, the zero point calibration of the pH electrode can be conducted. That is, by only intermittently heightening the flow rate of the carrier solution, the zero point calibration of the pH electrode can be automatically conducted.

The above gas sensor system of carrier solution flow-through type is a system in which the automation of the zero point calibration can be easily carried out, however, it still has the following problems. (1) When base line drift of the pH electrode is considerable, it is necessary that the zero point calibration is frequently carried out. (2) The drift of the zero point due to the temperature change can not be corrected.

SUMMARY OF INVENTION

The object of the present invention is to provide a carrier solution flow-through type gas sensor system by which the automation of the zero point calibration can be easily carried out, and the baseline drift and the temperature drift of the pH electrode can be compensated.

Accordingly, the gas sensor of the present invention is constructed in such a manner that: a gas exchange section having a gas exchanger which is provided with an inlet and an outlet to circulate a carrier solution including at least ions conjugate to a gas to be measured, and separated from the outside by the gas permeable membrane; a forward path section which is connected to the inlet of the gas exchanger and guides the carrier solution to the gas exchanger; a return path section which is connected to the outlet of the gas exchanger and guides the carrier solution from the gas exchanger to the outside; a reference pH electrode arranged inside the forward path section; and a measuring pH electrode arranged in either of the inside of the gas exchanger or the inside of the return path section, are provided.

Further, in the gas sensor, when it is constructed such that the reference pH electrode is arranged at a position separated from the inlet, in the inside of the forward path section, and the measuring pH electrode is arranged at a position separated from the outlet, in the inside of the return path section, because the gas exchange section is separated from each pH electrode, the gas exchange section is easily taken off and made to be disposable. Further, because each pH electrode is separated from the gas exchange section as described above, the periphery of the reference pH electrode and the measuring pH electrode can be kept at constant temperature by a thermostatted block.

On the one hand, in the gas sensor, when the measuring pH electrode is constructed such that it is arranged inside of the return path section in the vicinity of the outlet, it becomes a sensor with quick response.

Further, in the gas sensor, when the measuring pH electrode is constructed such that it is arranged inside of the gas exchanger, further, it becomes a sensor with quicker response.

Further, in the gas sensor system of the present invention, it is constructed such that any one of the gas sensors and the potential difference detection means between the measuring pH electrode and the reference pH electrode are provided. Further, in the gas sensor system, it is constructed such that a carrier solution supply means for supplying the carrier solution from the other end of the forward path section, and a flow control means for controlling the flow of the carrier solution are provided. Further, in the gas sensor system, it is constructed such that a gas partial pressure detection means for detecting the partial pressure of the gas to be measured according to the output of the potential difference detection means is provided.

Further, in the gas sensor, by using two ISFET as the reference pH electrode and the measuring pH electrode, and a pseudo-reference electrode, detection of source potentials of the reference pH electrode and measuring pH electrode based on the pseudo-reference electrode is available.

DETAILED DESCRIPTION OF PREFERRED EMBODIMENTS

Figure 8:
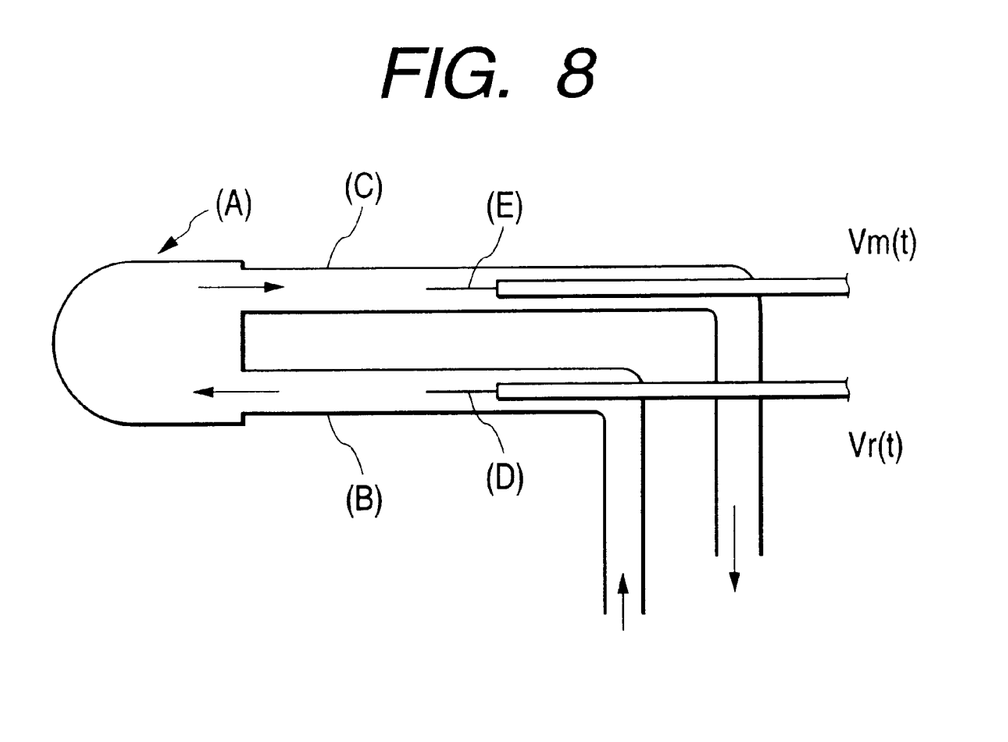
FIG. 8 is a view for explaining the principle of the gas sensor and the gas sensor system.

At first, the principle of the present invention will be described below. As shown in FIG. 8, to a gas exchange section (A) including a gas exchanger, a forward path section (B) and a return path section (C) to circulate the carrier solution are provided, and in the forward path section (B), a reference pH electrode (D) is provided, and in the return path section (C), a measuring pH electrode (E) is provided. The gas exchanger is separated from the outside by the gas permeable membrane. The carrier solution used herein, is a solution including ions conjugate to the gas to be measured.

The gas partial pressure measurement using such the gas sensor will be described below. Firstly, the gas exchanger (A) is inserted into a test substance. Next, the carrier solution is injected into the forward path section (B). According to this, the carrier solution is delivered from the forward path section (B) to the gas exchanger of the gas exchange section (A) and the return path section (C), and initially, its flow rate is heightened to a degree in which the gas exchange is not carried out in the gas exchanger. In this situation, a certain time t is set to t=0. In this case, the output potential of the reference pH electrode (D) is Vr(0), and the output potential of the measuring pH electrode (E) is Vm(0). Herein, the difference between them is found, and stored. That is, $\Delta V(0)$ expressed by the following expression (11) is read out, and stored. In this example, this processing is called zero point calibration.

$$\Delta V(0)=Vm(0)-Vr \quad (11)$$

Next, the carrier solution is slowly circulated at a constant speed, so that the gas exchange is fully conducted in the gas exchanger, and the difference between the output potential Vr(t) of the reference pH electrode (D) and the output potential Vm(t) of the measuring pH electrode (E) at the time t is read out. That is, $\Delta V(t)$ expressed by the following expression (12) is read out.

$$\Delta V(t)=Vm(t)-vr(t) \quad (12)$$

Herein, further, the difference between the previously stored $\Delta V(0)$ and $\Delta V(t)$ measured this time is found. That is, $\Delta\Delta V(t)$ expressed by the following expression (13) is found.

$$\Delta\Delta V(t)=\Delta V(t)-\Delta V(0) \quad (13)$$

This $\Delta\Delta V(t)$ can be regarded as a value which corresponds to the accurate gas partial pressure, not influenced by the electrode potential change due to the temperature change and the base line drift. The reason is as follows.

The expression (13) can be expressed as following.

$$\Delta\Delta V(t)=\Delta V(t)-\Delta V(0)=\{Vm(t)-Vm(0)\}-\{Vr(t)-Vr(0)\} \quad (14)$$

The change of the potential of each pH electrode at the time of measurement and the zero point calibration is generally expressed by the expression (15) (i=r, m).

$$Vi(t)-Vi(0)=\Delta pHi \times Si + \Delta Ti \times Ai + t \times Bi \quad (15)$$

Herein, the first, second and third terms of the right side respectively show the electrode potential change due to the pH change, temperature change, and base line drift at t=0–t. Herein, $\Delta pHi$ is a change of pH of the carrier solution at each electrode position, Si is the pH sensitivity of each pH electrode, $\Delta Ti$ is the temperature change of the carrier solution at each electrode position, Ai is a temperature coefficient of the potential change of each pH electrode, and Bi is the base line drift per unit time for each pH electrode. When the expression (15) is substituted into the expression (14), the expression (16) is obtained.

$$\Delta\Delta V(t)=\Delta pHm \times Sm - \Delta pHr \times Sr + \Delta Tm \times Am - \Delta Tr \times Ar + t \times (Bm-Br) \quad (16)$$

In this connection, because the pH of the carrier solution at the position at which the reference pH electrode (D) is provided, $\Delta pHr=0$ is regarded as constant. Further, when the electrodes with the same temperature coefficient and the same base line drift speed are used as the reference pH electrode (D) and the measuring pH electrode (E), and further, when these pH electrodes (D) and (E) are located close enough so that the temperature changes of both are made equal, the second and subsequent terms of the right side of the expression (16) become all zero, then, $$\Delta\Delta V(t)=\Delta pHm \times Sm. \quad (17)$$

On the one hand, because the relationship between the pH and the partial pressure (concentration) P of the gas to be measured is clear from the expression (3) and the expression (4), by obtaining $\Delta\Delta V(t)$, the change of the partial pressure of the gas $\Delta P$ can also be obtained together with the pH change $\Delta pHm$.

As described above, when the electrodes having characteristics close to each other are used as the measuring pH electrode and the reference pH electrode, the potential change due to the temperature change or the base line drift is cancelled, and as the result, only the potential change due to the pH change can be easily measured. In the known method (the above JP-B-4-017050) in which only the measurement electrode is used without using the reference pH electrode, the potential change during the time of the calibration and the measurement is expressed by the expression (15)(i=m), and it is difficult to exclude the potential change caused by other factors than the pH change. However, by the above sensor and system, this becomes easy.

Embodiments

Figure 1:
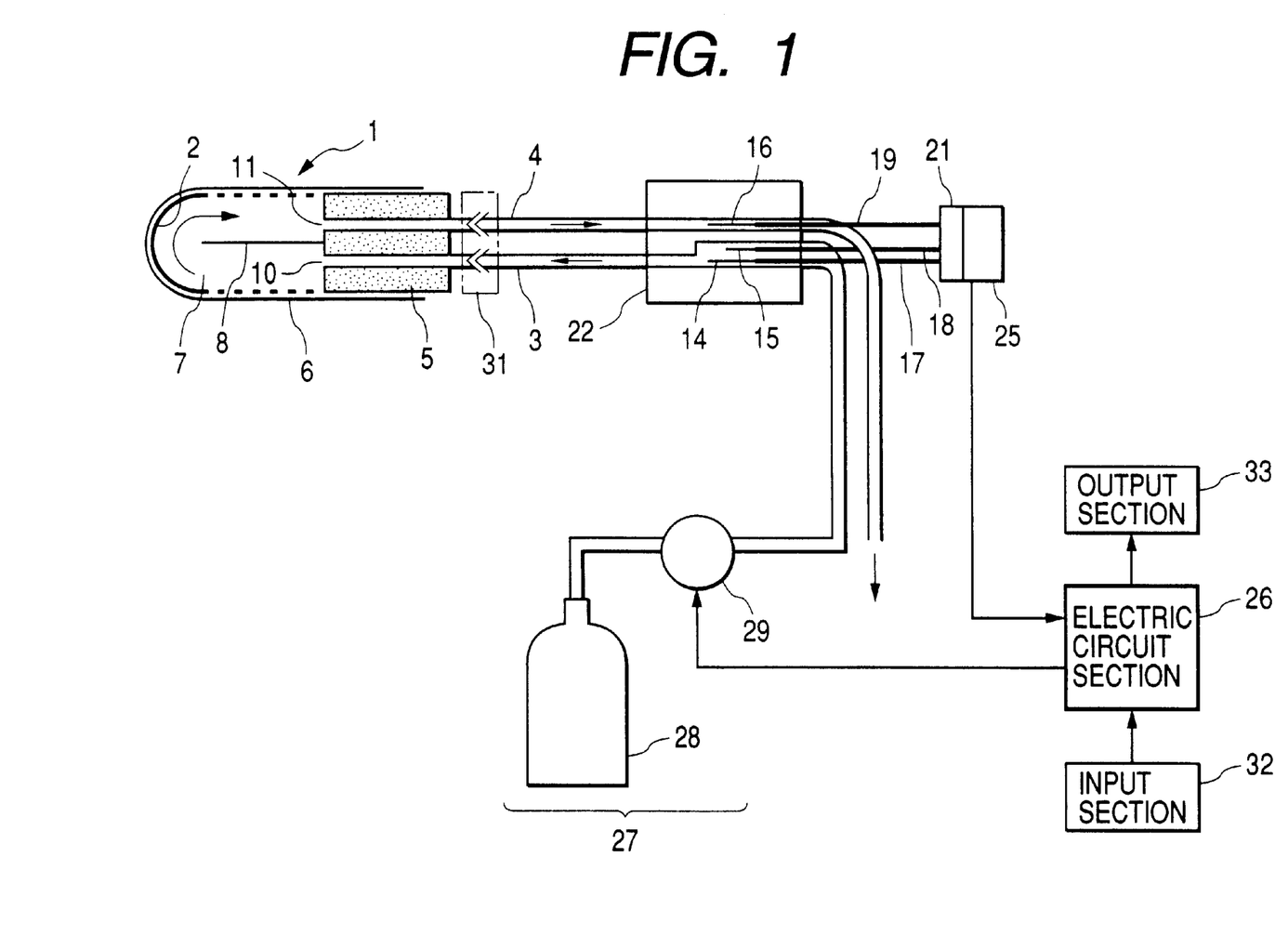
FIG. 1 is a structural view of a gas sensor system of the first embodiment.

In FIG. 1, the structure of the gas sensor system of the first embodiment of the present invention is shown. As shown in the drawing, a gas exchange section 1 is composed of a cylindrical body 2 having a semi-spherical bottom portion and a porous side portion, a connecting portion 5 which closes an opening portion of the cylindrical body 2 and holds one end of a conduit tube 3 and a conduit tube 4, and communicates their insides to the inside of the cylindrical body 2, and a gas permeable membrane 6 which covers the cylindrical body 2. Herein, the inside of the cylindrical body 2 is a gas exchanger 7. In the present example, the connecting portion 5 has 2 through holes, and a conduit tube 3 and the conduit tube 4 are respectively engaged with each of them, and one end of those conduit tube 3 and conduit tube 4 is extended to reach the gas exchanger 7. Therefore, one end of the conduit tube 3 and one end of the conduit tube 4 respectively form the inlet 10 and outlet 11 of the gas exchanger 7. Accordingly, in the present example, the conduit tube 3 is a forward path section, and the conduit tube 4 is a return path section. As the gas permeable membrane 6, a silicon rubber homogeneous film having good gas transmitting property, or a hydrophobic porous film such as porous teflon or polypropylene, is preferable. In this connection, a partition plate 8 is provided in order to increase the length of the flow path so that the gas exchange is fully conducted in the inside of the gas exchanger 7. To the conduit tube 3 and the conduit tube 4, a connector 31 is provided in the vicinity of the gas exchange section 1, and the system is made attachable and detachable here.

The reference pH electrode 14 and a pseudo-reference electrode 15 are provided inside the conduit tube 3 at the position separated from the gas exchanger 7. On the one hand, the measuring pH electrode 16 is provided inside the conduit tube 4 at the position separated from the gas exchanger 7. Respective one end side of lead wires 17, 18 and 19 are connected to the reference pH electrode 14, pseudo-reference electrode 15 and measuring pH electrode 16. These are guided to the outside under the situation that the inside of the conduit tube 3 and the conduit tube 4 is kept liquid-tight condition, and the other end sides of them are connected to a socket 21.

A thermostatted block 22 is provided so that a portion of the conduit tube 3 having the reference pH electrode 14 and the pseudo-reference electrode 15 therein, and a portion of the conduit 4 having the measuring pH electrode 16 therein, are made at constant temperature. The inside temperature of the thermostatted block 22 is set to a bodily temperature of the subject for whom the sensor system is used.

The socket 21 is detachable to the connector 25. The system is constructed in such a manner that each of the potential detected from the reference pH electrode 14, the pseudo-reference electrode 15 and the measuring pH electrode 16 enters into an electric circuit section 26 through these socket 21 and connector 25.

A carrier solution supply means 27 is provided at the other end of the conduit tube 3, and the carrier solution is supplied to the conduit tube 3. The carrier solution supply means 27 is composed of a carrier solution container 28 and a feed solution pump 29.

The electric circuit 26 has a data processing function to conduct predetermined processing according to each potential detected from the reference pH electrode 14, pseudo-reference electrode 15 and measuring pH electrode 16, and a function to control the feed solution pump 29 and control the flow of the carrier solution. To the electric circuit 26, an input section 32 constructed by, for example, a key board to input various instructions, and an output section 33 constructed by, for example, a printer or a display section to output the result of the data processing, are connected.

Figure 2:
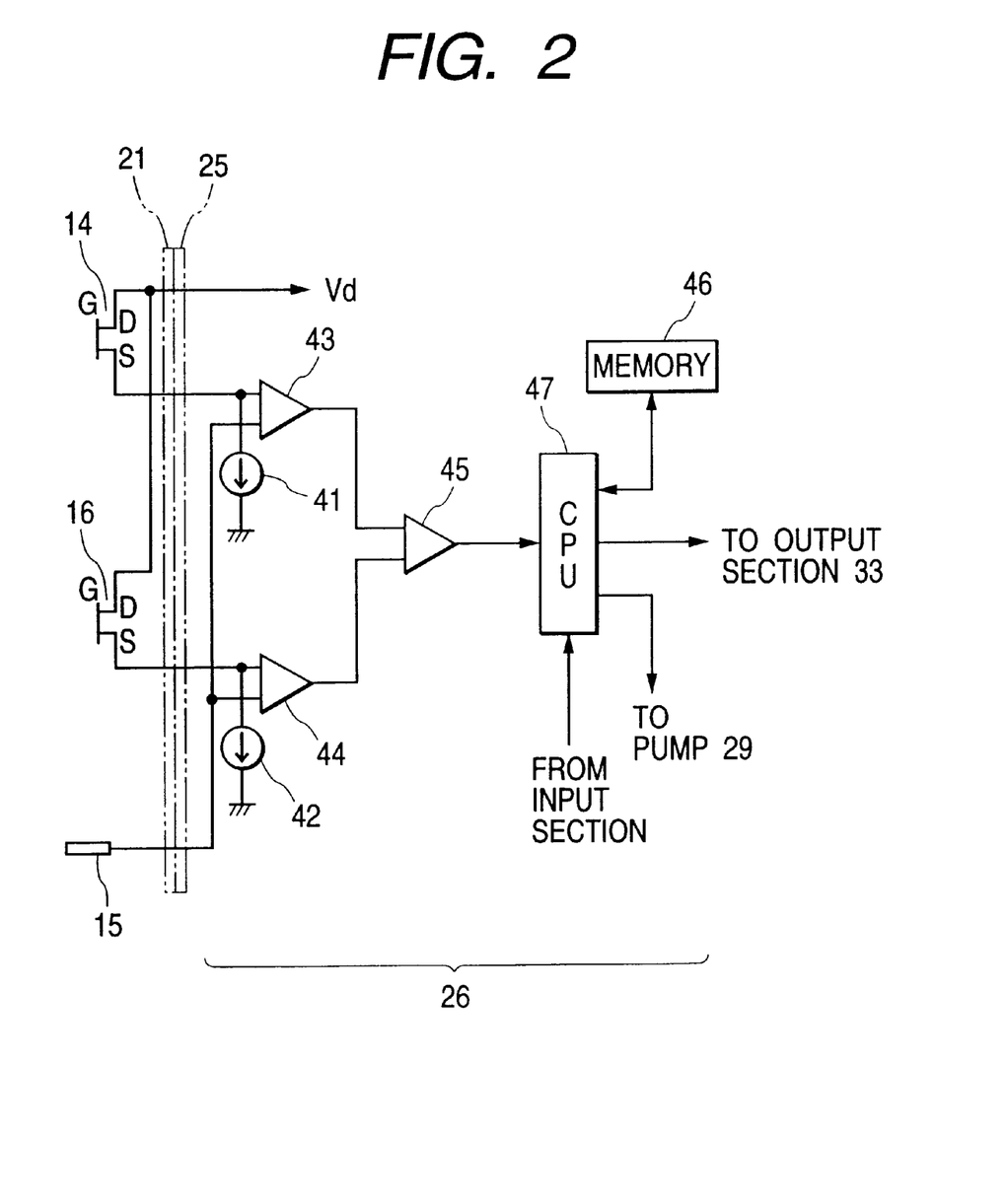
FIG. 2 is a view showing a signal processing circuit of the system shown in FIG. 1.

In the present example, both of the reference pH electrode 14 and the measuring pH electrode 16 are chosen of the type Ion-Sensitive Field-Effect-Transistor (ISFET). These are ones whose temperature characteristic or drift characteristic is close to each other. A signal processing circuit of the gas sensor system is shown in FIG. 2. This drawing shows a situation that the socket 21 is connected to the connector 25. The electric circuit section 26 has: a constant current circuits 41, 42, to supply the same constant current to source terminals of the reference pH electrode 14 and the measuring pH electrode 16; operation amplifiers 43, 44 to detect the source potential of the reference pH electrode 14 and the measuring pH electrode 16 whose common reference is a pseudo-reference electrode 15; a differential amplifier 45 to detect and amplify the differential voltage of these output voltage signals; and a CPU 47 to take-in the output voltage signal after digitizing it, and to calculate the pH value and further, the gas partial pressure in the cooperation with a memory 46, following to the instruction from the input section 32.

Next, referring to the structural drawing in FIG. 1 and FIG. 2, and a flow chart in FIG. 3, the operation of the present system will be described.

Firstly, the operator inserts the gas exchange section 1 into a test substance. The test substance may be the liquid phase such as, for example, the blood, or the gas phase. For example, when the gas partial pressure of the organ such as the stomach, esophagus, oral cavity, nasal cavity, blood vessel, urethra, etc. is measured, the gas exchange section 1 is positioned in the objective organ.

When the present system starts the operation, the CPU 47 judges whether the instruction of the zero point calibration is input from the input section 32 (step 101), and further, whether the instruction of the measurement is input from the input section 32 (step 102). Herein, when the operator inputs the instruction of the zero point calibration, the CPU 47 controls the feed solution pump 29, and makes the speed of the carrier solution to be flowed into the conduit tube 3 at a predetermined high speed (step 103). Accordingly, in the gas exchange section 1, the contact time of the carrier solution with gas permeable membrane becomes extremely short, and results in a condition that the pH of the carrier solution of the conduit tube 3 and the conduit tube 4 is almost the same. In this condition, the CPU 47 conducts the zero point calibration (step 104). That is, the CPU 47 writes the output voltage $\Delta V(0)$ of the differential amplifier 45 at this time, on the memory 46.

Next, the operator inputs the instruction of the measurement. According to this, the CPU 47 controls the feed solution pump 29 and makes the speed of the carrier solution to be flowed in the conduit tube 3 at a predetermined low speed or make the carrier solution stop during predetermined period (step 105). Thereby, in the gas exchange section 1, the contact time of the carrier solution with gas permeable membrane becomes long, and the gas exchange is fully conducted. Next, the CPU 47 finds the difference $\Delta\Delta V(t)$ by using the output voltage $\Delta V(t)$ of the differential amplifier 45 at that time t, and the $\Delta V(0)$ written on the memory 46, and from this, finds $\Delta pHm$ by using the relationship of the expression (17), and further, finds the change of the gas partial pressure $\Delta P$ by using the relationship of the expressions (3) or (4) (step 106).

The CPU 47 displays or prints the pH measurement value $\Delta pHm$, and the gas partial pressure measurement value $\Delta P$ (step 107). Next, the CPU 47 judges whether there is an instruction of the measurement completion from the input section 32 (step 108). Until this instruction comes to the CPU 47, the CPU 47 repeats the steps of the measurement 106, 107, and when the instruction of the measurement completion comes to the CPU 47, the sequence returns to the initial step 101.

According to the present embodiment, because the reference pH electrode 14, pseudo-reference electrode 15 and measuring pH electrode 16 are separately arranged from the gas exchanger 7, these pH electrodes 14 and 16 can be arranged in the thermostatted block 22, and the temperature can be set to the same temperature as in the test substance. Therefore, the accuracy in measurement can be increased. Further, when the gas exchange section 1 can be separated by the connector 31, and the gas exchange section 1 is made disposable.

Figure 3:
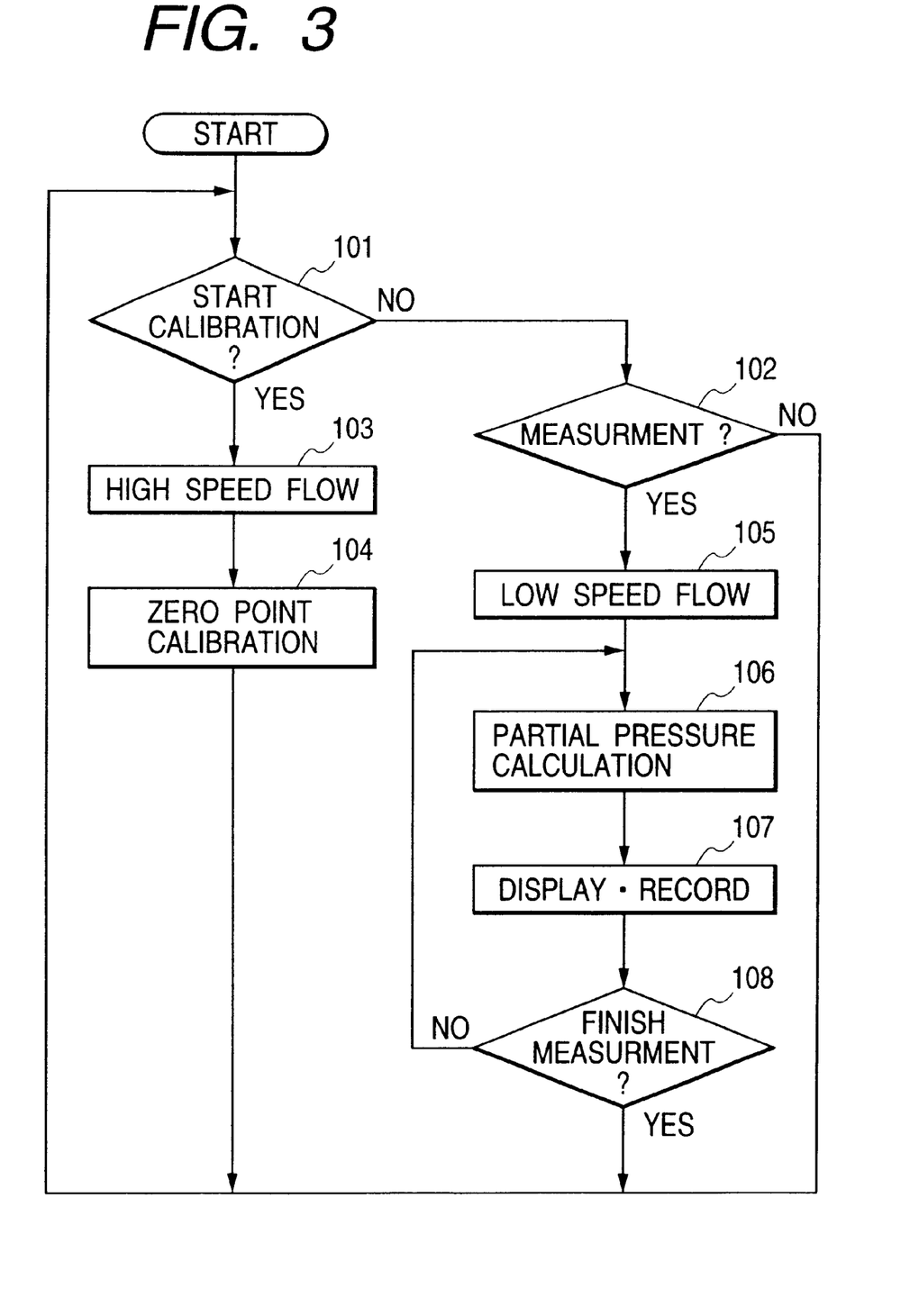
FIG. 3 is a view for explaining operations of the system shown in FIG. 1.

In the present example, as shown in flow chart in FIG. 3, the CPU 47 waits the instruction of the operator and conducts the processing such as the zero point calibration or the measurement, however, when the CPU 47 determines the timing of them according to the program, all of the zero point calibration and the measurement can be conducted automatically.

Further, in the present example, the carrier solution is continuously flowed during the measurement time, however, this flow may be intermittent. In this case, the system is controlled so that the carrier solution is made to flow at a predetermined time interval, and when the flow stops, gas exchange of the carrier solution can be fully conducted in the gas exchanger 7, and the carrier solution comes to the position of the measuring pH electrode 16. According to this intermittent flow control, it is not necessary that the feed solution pump 29 makes the carrier solution flow at an extremely slow predetermined speed. Instead of that, only the repetition of flowing at a predetermined speed and stopping is required, enabling the structure of the feed solution pump 29 simple.

Figure 4:
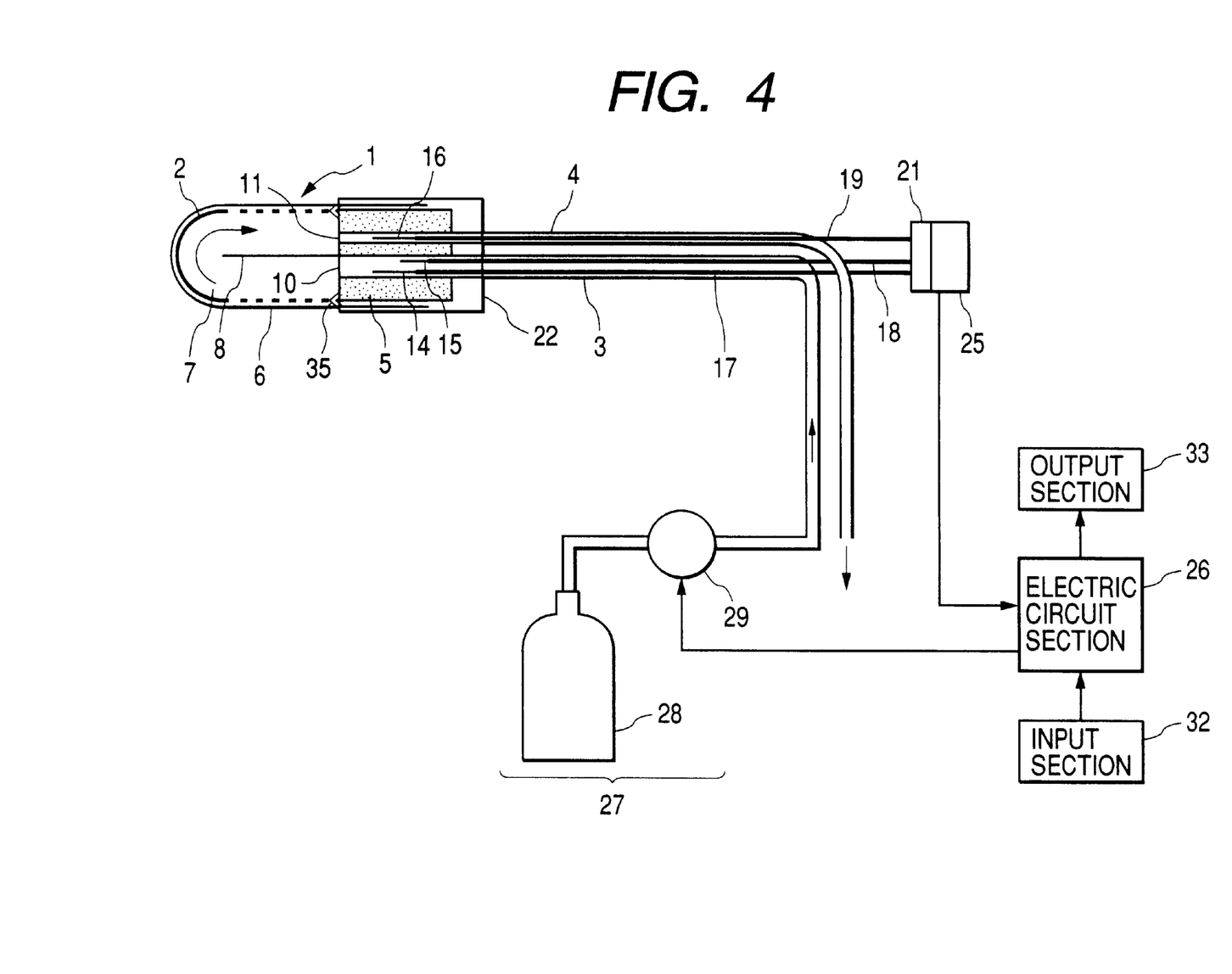
FIG. 4 is a structural view of a gas sensor system of the second embodiment.

The structure of the gas sensor system of the second embodiment of the present invention will be shown in FIG. 4. The same component as each component shown in FIG. 1 is denoted- by the same number. The different points of this system from the above mentioned system are that all of the reference pH electrode 14, pseudo-reference electrode 15 and the measuring pH electrode 16 are arranged in the vicinity of the gas exchanger 7, and that the whole gas exchange section 1 is not detachable, but the cylindrical body 2 forming the gas exchanger 7 is detachable from the connection section 5. In the present example, all of the reference pH electrode 14, pseudo-reference electrode 15 and the measuring pH electrode 16 are arranged in the connection section 5. Further, the connection section 5 is in the thermostatted block 22. Further, the cylindrical body 2 is detachable from the connection section 5 by the connector 35.

The control of the flow of the carrier solution and the processing of the output potential of each of electrodes 14, 15 and 16 in the present embodiment are the same as in the first embodiment.

According to the present embodiment, because the measuring pH electrode 16 is arranged in the vicinity of the gas exchanger 7, the response time is excellent. That is, the change of the partial pressure of the gas of the test substance can be quickly detected. Further, because the cylindrical body 2 can be removed together with the gas permeable membrane 6, this portion can be easily made disposable, and post-processing is simple.

Further, because the reference pH electrode 14, pseudo-reference electrode 15 and measuring pH electrode 16 are separately arranged from the gas exchanger 7, these pH electrodes 14 and 16 can be arranged in the thermostatted block 22, and the temperature of them can be set to the same temperature as that in the test substance. Therefore, the measurement accuracy can be increased.

Figure 5:
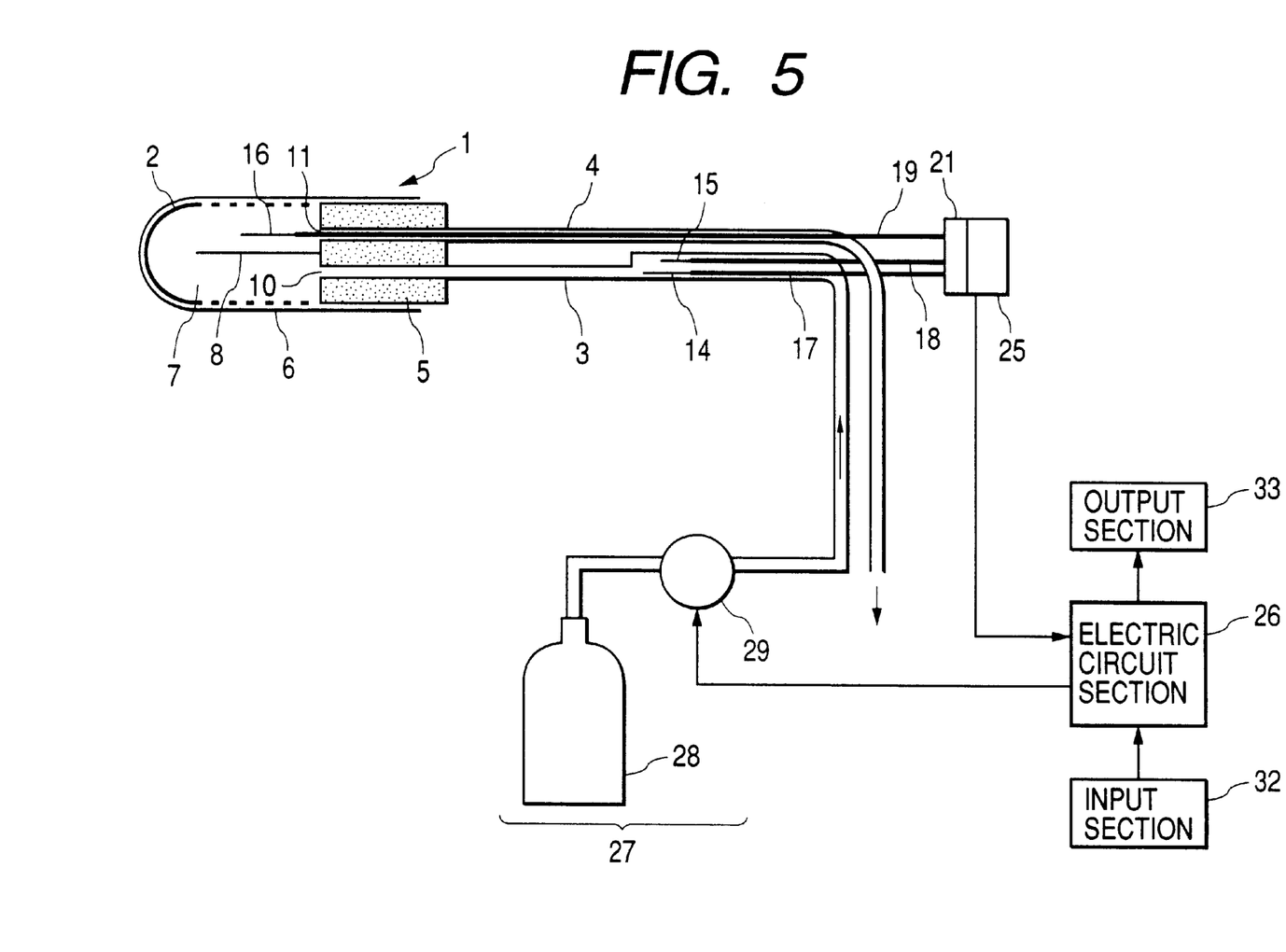
FIG. 5 is a structural view of a gas sensor system of the third embodiment.

The structure of the gas sensor system of the third embodiment of the present invention will be shown in FIG. 5. The same component as each component shown in FIG. 1 is denoted by the same number. The different points of this system from the above system are that the measuring pH electrode 16 is arranged in the gas exchanger 7, and that the thermostatted block 22 and the connector 31 are not provided.

The control of the flow of the carrier solution and the processing of the output potential of each of electrodes 14, 15 and 16 in the present embodiment are the same as in the first embodiment. However, in the present embodiment, even when the flow of the carrier solution is stopped during the measurement time, the measuring pH electrode 16 continuously outputs the measurement potential. Also according to this, the pH in the test substance, and further, the partial pressure of the gas can be measured.

According to the present embodiment, because the measuring pH electrode 16 is arranged in the gas exchanger 7, the response is further better than the second embodiment.

Figure 6:
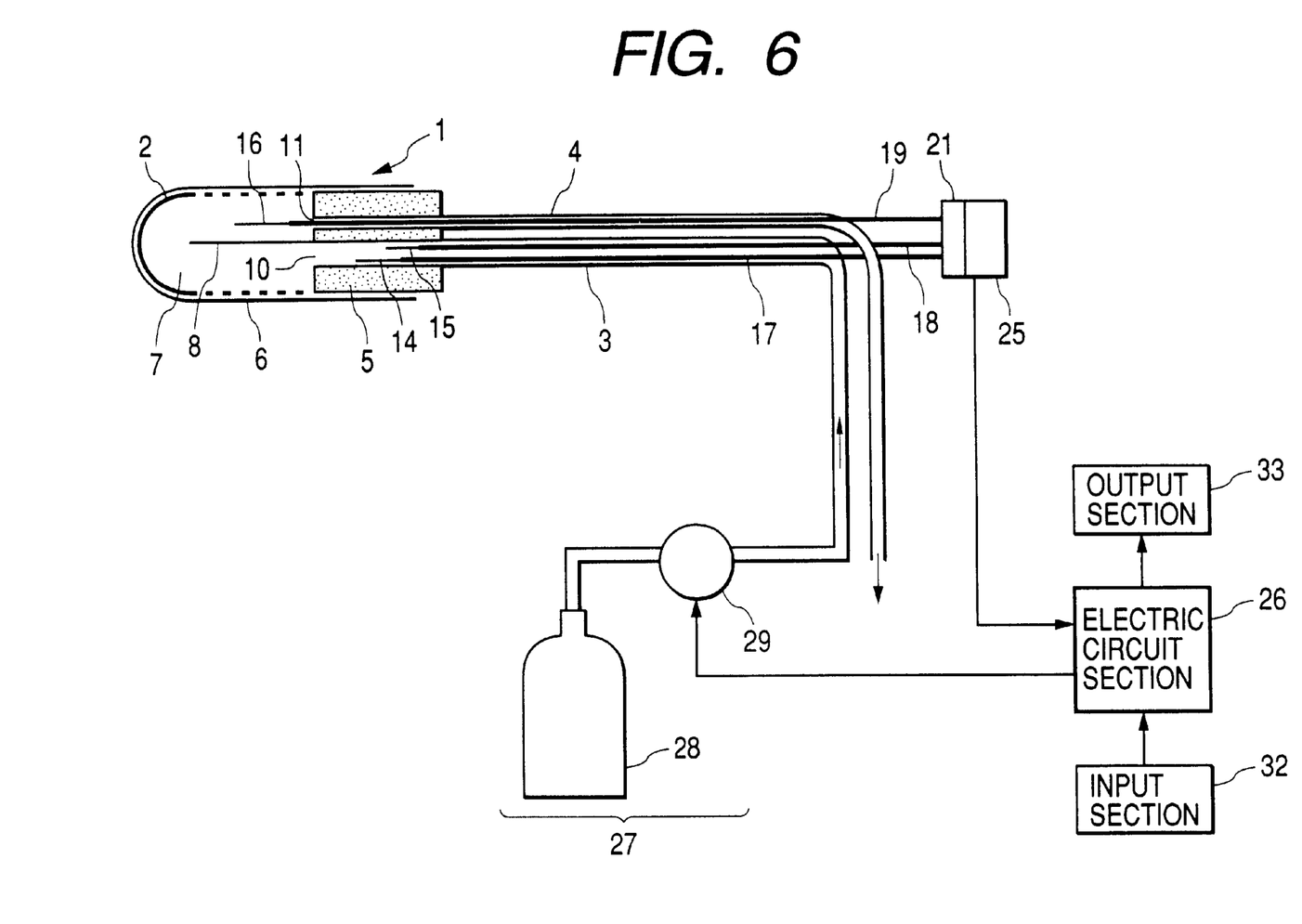
FIG. 6 is a structural view of a gas sensor system of the fourth embodiment.

The structure of the gas sensor system of the fourth embodiment of the present invention will be shown in FIG. 6. The different point of this system from the third embodiment is a point that the reference pH electrode 14 and pseudo-reference electrode 15 are arranged in the vicinity of the inlet 10 of the gas exchanger 7. Also according to this, the same effect as the third embodiment can be obtained, however, because the reference pH electrode 14 and the measuring pH electrode 16 are close to each other, the temperature difference of the solution around both is small, and the more accurate measurement result is obtained. However, in this case, when the flow of the carrier solution is stopped during the measurement, because the reference pH electrode 14 is close to the gas exchanger 7, there is a possibility that its output potential is influenced by the carrier solution after the exchange of the gas. Accordingly, in the present embodiment, the carrier solution is made to continuously flow during the measurement.

Figure 7:
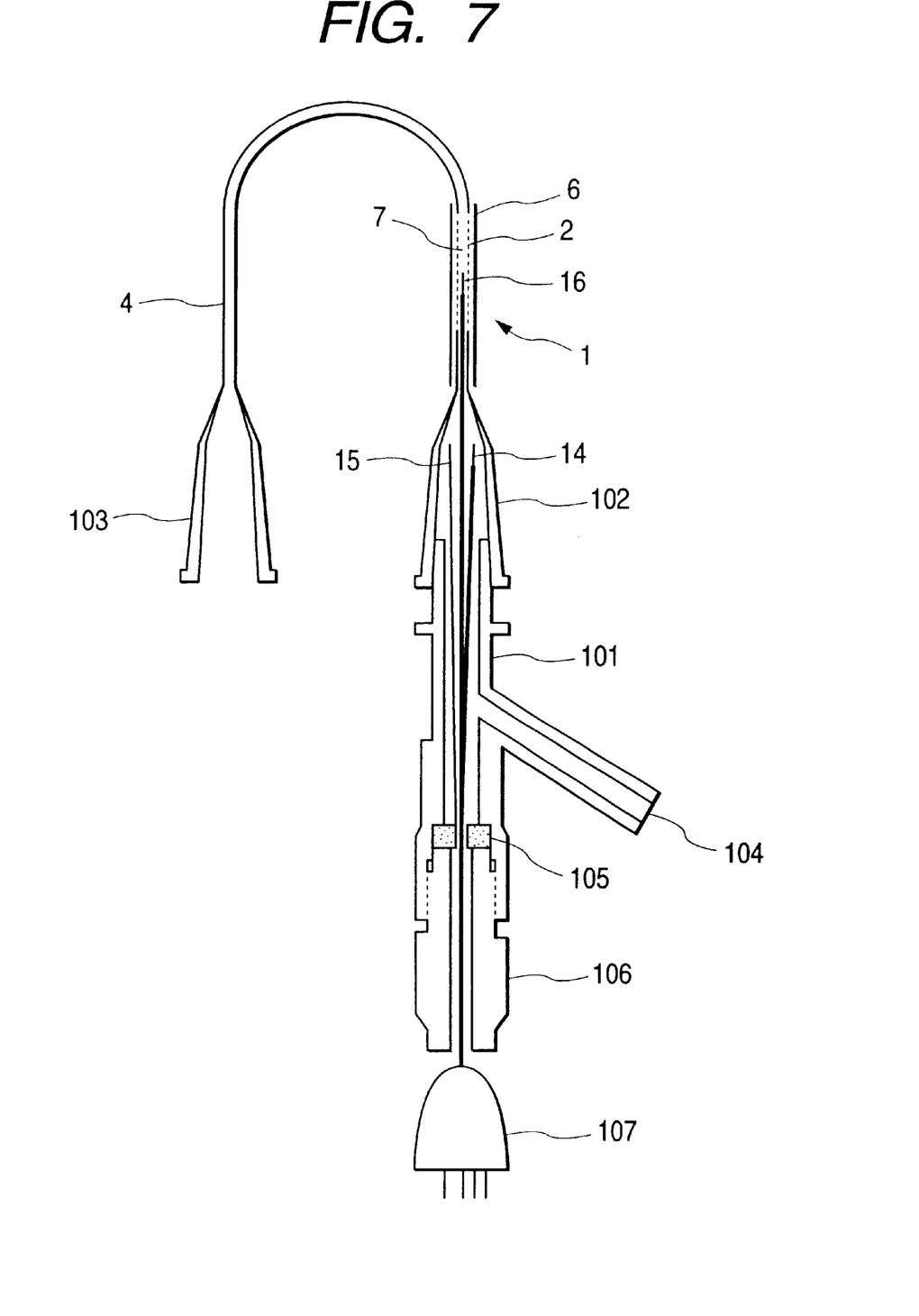
FIG. 7 is a structural view of a gas sensor system of the fifth embodiment.

The structure of the gas sensor system of the fifth embodiment of the present invention will be shown in FIG. 7. The different point of this system from the above system described in the first to fourth embodiments is that a flow path for carrier solution arranged in gas exchange section 1 is linearly provided instead of being folded. In the reference pH electrode 14, the pseudo-reference electrode 15 and the measuring pH electrode 16, one ends thereof are connected at a sensor connector 107. The three electrodes 14,15 and 16 are arranged in each hollow portion of a O-ring engagement portion 106, a sensor body 101 and a carrier solution inlet to gas exchanger 102. The reference pH. electrode 14 and the pseudo-reference electrode 15 are arranged in a carrier solution inlet to gas exchanger 102, and the measuring pH electrode 16 is arranged in the gas exchanger 7 in the cylindrical body 2. In the sensor body 101 at a side of the sensor connector 107, the O-ring 105 fixes the three electrodes 14,15 and 16 air tightly by pressure of the O-ring engagement 106 having a screw structure. The carrier solution poured from a carrier solution inlet to sensor body 104 of the sensor body 101 passes through the sensor body 101, the carrier solution inlet to gas exchanger 102, the gas exchange section 1, and the conduit tube (return path)4. Then, it is discharged from a carrier solution outlet from gas exchanger 103. At this time, the flow path defined from the sensor body 101 to the gas exchange section 1 serves as the forward path. In FIG. 7, the carrier solution supply means is omitted as well as the feed solution pump 29, the output section 33, the electric circuit section 26 and the input section 32.

In each of the above embodiments, as the reference pH electrode 14 and the measuring pH electrode 16, ISFET is used. Because ISFET is easily made to a very small size, and the pH response time is short, it is suitable for the gas sensor of the present system. Further, in the ISFET, a large amount of elements having uniform characteristic can be produced from a sheet of silicon wafer, so from a point that each characteristic of the measurement side electrode and the reference side electrode is easily made uniform, it is suitable as the pH electrode of the present system. However, each kind of known electrode such as a glass electrode can also be used as the pH electrode.

On the one hand, the metal such as gold, silver, platinum, or an electric conductor such as carbon or the other material, is used as the pseudo-reference electrode 15.

And the pseudo-reference electrode 15 may be arranged inside either the gas exchange section, the forward path section 3, or the return path section 4 just for detecting the source potentials of the reference pH electrode and the measuring pH electrode based on the output of the pseude-reference electrode.

As the carrier solution, as described above, a solution including conjugate ions to the gas to be measured is used. For example, when the object to be measured is the carbon dioxide, the solution including bicarbonate ions is used, and when it is the ammonia gas, the solution including ammonium ions is used. Further, in order to secure the electric conductivity of the carrier solution, the electrolyte such as sodium chloride or potassium chloride may be added to it.

According to the present invention, the following advantages are obtained.

(1) The Frequency of the Calibration Can be Reduced.

In the conventional method in which the measuring pH electrode and the reference electrode are used, when the base line drift of the measuring pH electrode occurs, the zero point calibration is frequently necessary. However, in the present invention, by using the pH electrodes having the close drift characteristic for the measurement and the reference, the base line drift is cancelled, and the zero point calibration frequency can be reduced.

(2) The Temperature Compensation is Simple.

In the same manner, by using the pH electrodes having the close temperature coefficients for the measurement and the reference, the shift of the zero point due to the temperature change can be cancelled.

(3) The Dry Preservation of the Gas Sensor is Possible, and the Maintenance Becomes Easy.

In the conventional method, the reference electrode having the stable potential is necessary. Therefore, it is inevitable that the liquid-junction type reference electrode such as the saturated calomel electrode is used. In this case, the wet preservation is absolutely necessaryas well as the replenishment of the inner solution. However, in the gas sensor of the present invention, the pseudo-reference electrode is used instead of the reference electrode, and this may simply be a metallic wire. This is for the reason that, in the gas sensor system of the present invention, because the potential difference between the measurement electrode and the reference electrode is usesd, there is no problem even when the electrode potential of the pseudo-reference electrode is changed. When the ISFET is used as the pH electrode, the gas sensor can be perfectly made dry.

What is claimed is:

1. A gas sensor comprising:
   a gas exchange section including a gas exchanger having an inlet and an outlet for circulating a carrier solution including at least ions conjugate to a gas to be measured, and the gas exchanger isolated from any location disposed external to the gas sensor by a gas permeable membrane;
   a forward path section connected to the inlet of the gas exchanger and for guiding the carrier solution to the gas exchanger;
   a return path section connected to the outlet of the gas exchanger and for guiding the carrier solution from the gas exchanger to a location disposed external to the gas sensor;
   a reference pH electrode arranged inside the forward path section; and
   a measuring pH electrode arranged inside either the gas exchanger or the return path section.

2. The gas sensor according to claim 1, wherein the reference pH electrode is arranged inside of the forward path section at a position separated from the inlet, and the measuring pH electrode is arranged inside of the return path section at a position separated from the outlet.

3. The gas sensor according to claim 2, wherein a constant temperature means for making the temperature of the reference pH electrode and the measuring pH electrode constant, is provided.

4. The gas sensor according to claim 1, wherein the measuring pH electrode is arranged inside of the return path section in the vicinity of outlet.

5. The gas sensor according to claim 1, wherein the measuring pH electrode is arranged inside of the gas exchanger, and the reference pH electrode is arranged adjacent to the inlet of the gas exchanger.

6. The gas sensor according to claim 1, wherein a flow path of the carrier solution is folded in the gas exchanger to position the gas exchange section at the tip end of the sensor.

7. A gas sensor comprising:
   a gas exchange section including a gas exchanger having an inlet and an outlet for circulating a carrier solution including at least ions conjugate to a gas to be measured, and the gas exchanger isolated from any location disposed external to the gas sensor by a gas permeable membrane;
   a forward path section connected to the inlet of the gas exchanger for guiding the carrier solution to the gas exchanger;
   a return path section connected to the outlet of the gas exchanger for guiding the carrier solution from the gas exchanger to a -location disposed external to the gas sensor;
   a reference pH electrode arranged inside the forward path section; and
   a measuring pH electrode arranged inside the gas exchanger,
   wherein the inlet and outlet are linearly provided in the gas exchanger.

8. A gas sensor system according to claim 1, further comprising:
   a potential difference detection means for detecting the potential difference between the measuring pH electrode and the reference pH electrode.

9. The gas sensor system according to claim 8, further comprising:
   a carrier solution supply means for supplying the carrier solution from the other end of the forward path section; and
   a flow control means for controlling the flow of the carrier solution.

10. The gas sensor system according to claim 8, further comprising:
    a gas partial pressure detection means for detecting the partial pressure of a gas to be measured according to the output of the potential difference detection means.

11. The gas sensor according to claim 1, wherein said reference pH electrode and said measuring pH electrode are both selected as a type ISFET, and further comprising:
    a pseudo-reference electrode for detecting source potentials of said reference pH electrode and said measuring pH electrode based on the output of said pseudo-reference electrode, inside either said gas exchange section, said forward path section or said return path section.

12. The gas sensor according to claim 7, wherein said reference pH electrode and said measuring pH electrode are both selected as a type ISFET, and further comprising:
    a pseudo-reference electrode for detecting source potentials of said reference pH electrode and said measuring pH electrode based on the output of said pseudo-reference electrode, inside either said gas exchange section, said forward path section or said return path section.

* * * * *